United States Patent

Kientsch-Engel et al.

[11] Patent Number: 5,863,740
[45] Date of Patent: Jan. 26, 1999

[54] INTERFERENCE ELIMINATING AGENT FOR APPLICATION IN IMMUNOASSAYS

[75] Inventors: Rosemarie Kientsch-Engel, Feldafing; Frederic Donie; Michael Wiedmann, both of Penzberg, all of Germany

[73] Assignee: Boehringer Mannheim GmbH, Mannheim, Germany

[21] Appl. No.: 700,435

[22] PCT Filed: Mar. 3, 1995

[86] PCT No.: PCT/EP95/00776

§ 371 Date: Sep. 5, 1996

§ 102(e) Date: Sep. 5, 1996

[87] PCT Pub. No.: WO95/23801

PCT Pub. Date: Sep. 8, 1995

[30] Foreign Application Priority Data

Mar. 5, 1994 [DE] Germany .................. 44 07 423.9
Feb. 25, 1995 [WO] WIPO .............. PCT/EP95/00690

[51] Int. Cl.$^6$ .................................................. G01N 33/53
[52] U.S. Cl. ................... 435/7.5; 435/7.1; 435/7.2; 435/7.92; 435/962; 435/172.1; 436/175; 436/824; 436/825
[58] Field of Search .................. 435/7.1, 7.2, 7.5, 435/7.92, 962, 172.1; 436/175, 824, 825

[56] References Cited

U.S. PATENT DOCUMENTS

| 4,562,157 | 12/1985 | Lowe et al. | 435/287.2 |
|---|---|---|---|
| 4,839,293 | 6/1989 | Cantor et al. | 435/357 |
| 5,212,063 | 5/1993 | Ofenloch-Hähnle | 435/7.5 |
| 5,252,466 | 10/1993 | Cronan, Jr. | 435/69.7 |
| 5,252,743 | 10/1993 | Barrett et al. | 548/303.7 |
| 5,260,004 | 11/1993 | Samuelson et al. | 264/104 |
| 5,268,306 | 12/1993 | Berger et al. | 436/527 |
| 5,474,796 | 12/1995 | Brennan | 427/2.13 |
| 5,482,867 | 1/1996 | Barrett et al. | 436/518 |
| 5,487,975 | 1/1996 | Miller et al. | 435/7.5 |
| 5,489,528 | 2/1996 | Kopetzki et al. | 435/252.3 |
| 5,528,338 | 6/1996 | Goldenberg | 424/178.1 |
| 5,643,731 | 7/1997 | Bosslet | 435/7.1 |

FOREIGN PATENT DOCUMENTS

| 0198015 | 1/1985 | European Pat. Off. |
|---|---|---|
| 0155854 | 3/1985 | European Pat. Off. |
| 3800644 | 7/1989 | Germany . |

OTHER PUBLICATIONS

Gitlin et al, Biochem. J. 1990, 269, p. 527–530.
Mullen W. et al, Science, vol. 262, 10 Dec. 1993, pp. 1706–1708.
Gitlin et al. "Studies on the Biotin–Biotin Sites of Avidin and Streptavidin" Biochem Journal, 1990 vol. 269 pp. 527–530.
Wilchek et al "The Avidin–Biotin Complex in Bioanalytical Applications" Analytical Biochemistry vol. 171, 1988, pp. 1–32.

Primary Examiner—James C. Housel
Assistant Examiner—Ginny Allen Portner
Attorney, Agent, or Firm—Nikaido Marmelstein Murray & Oram, LLP

[57] ABSTRACT

The invention concerns interference-eliminating agents for avoiding unspecific interactions in immunoassays in which avidin or streptavidin or a derivative thereof are used as the interference-eliminating agents.

25 Claims, 1 Drawing Sheet

INTERFERENCE ELIMINATING AGENT FOR APPLICATION IN IMMUNOASSAYS

This Application is a 371 of PCT/EP95/00776, filed Mar. 3, 1995, which claims foreign priority to German Application P 44 07 423.9, filed Mar. 5, 1994.

The invention concerns avidin or streptavidin or a derivative thereof as an interference-eliminating agent in immunoassays as well as methods for the detection of an analyte using this interference-eliminating agent.

Immunological methods of detection have become of great importance in recent years. They can be used to rapidly and accurately detect the presence of drugs, hormones, proteins, infectious organisms and in particular specific antibodies in biological samples. In all immunological methods of detection a specific binding reaction occurs between a first specific binding partner, the substance which it is intended to detect ("analyte") and a second specific binding partner which reacts specifically with the analyte or binds it. In this process the analyte and specific analyte binding partner, the so-called partners of a specific binding pair, form a specific binding pair which is in general a complex between an antigen and an antibody or antibody fragment. In this connection it is possible for more than one analyte or binding partner to react with one another in each reaction. These specific binding reactions are detected in various ways. In general one participant in the specific binding reaction is labelled. Common labelling methods are radioisotopes, chromogens, fluorogens, enzyme labels or substances which in turn can form a specific binding pair (e.g. biotin/streptavidin). In heterogeneous immunoassays one of the binding partners is immobilized on a solid phase.

A serious problem in immunoassays is that undesired interactions and unspecific binding reactions can occur between specific binding partners of the immunoassay and the sample, additional constituents present in the sample and under certain circumstances in the solid phase. Such interactions usually cause an increase of the background signal and also a larger scattering of the signals and thus a reduced sensitivity and specificity of the test concerned. False-positive measurements can also result from an unspecific interaction with the labelled binding partner as well as from the specific binding of test components by sample constituents i.e. as a result of the falsely-increased measured signal it is assumed that an analyte is present even when it is absent.

Many attempts have been made to reduce these unspecific interactions in immunoassays. It has been known for a long time that various carbohydrate components and various proteins, protein mixtures or protein fractions as well as hydrolysates thereof can reduce unspecific interactions between the test components and the analyte in immunoassays (for example Robertson et al., Journal of Immun. Meth. 26, 1985, 195; EP-A-260903; U.S. Pat. No. 4,931,385). The use of crude protein fractions and crude hydrolysates has the disadvantage that the constituents contained therein can in turn cause other interferences of the test. Moreover hydrolysates produced by enzymatic means may be contaminated with the proteases used for their manufacture and usually do not have a uniform quality since the cleavage is difficult to control. Protease contaminations can attack test components and lead to an impairment of the test functions and storage stability even in low amounts.

The use of chemically modified proteins, in particular of succinylated or acetylated proteins, has also been described for the reduction of unspecific interactions in immunoassays (U.S. Pat. No. 5,051,356; EP-A-0 525 916). However, it was not possible to avoid many of the false positive results in tests for antibodies from serum with these substances.

EP-A-0 331 068 and WO 91/06559 describe the use of polymerized immunoglobulins, in particular IgG, to reduce specific interfering factors such as e.g. rheumatoid factors. However, they do not enable all interfering interactions to be satisfactorily eliminated. Moreover, the addition of unspecific human immunoglobulin (monomeric or polymeric antibodies or fragments thereof) in tests for human antibodies can lead to an increase in the blank. Furthermore the production of human or animal IgG is time-consuming and expensive.

The object of the invention was therefore to provide new interference-eliminating substances and interference-eliminating agents which reduce interference by unspecific interactions in immunoassays which is better than that known from the state of the art. Unspecific interactions are understood as all interactions between components of the process which can lead to falsifications of the measured result. The interference-eliminating substances should avoid false-positive analytical results in particular in the analysis of antibodies. In particular it is intended to avoid interference when using avidin or streptavidin as a binding partner in an immunoassay.

This object was achieved by avidin or streptavidin or derivatives thereof as interference-eliminating agents. The use of these substances surprisingly resulted in an elimination of interference in assays in particular in assays in which avidin or streptavidin is used as a binding partner.

The invention therefore concerns interference-eliminating agents to avoid unspecific interactions in assays which contain avidin or streptavidin or derivatives thereof and the use of these interference-eliminating agents in assays. Avidin or streptavidin or derivatives thereof are used in a soluble form according to the invention. They are not bound or coupled to a solid phase or a marker group such as an enzyme. The interference-eliminating agent according to the invention is always used in addition to the reagents that are otherwise necessary for the test and does not become a component of the complex which forms during the course of the test reaction composed of analyte to be detected and specific binding partners. The interference-eliminating agent according to the invention is preferably used in immunological tests (immunoassays). It can, however, also be used in tests which are based on other interactions such as nucleic acid tests. The interference-eliminating agent is preferably used in tests in which one test component is bound to avidin or streptavidin such as an avidin-coated or streptavidin-coated solid phase in the case of immunological or nucleic acid tests. Avidin or streptavidin are understood as the naturally occurring purified proteins or recombinant avidin or streptavidin. Avidin or streptavidin derivatives are understood as modified avidin or streptavidin molecules. The modification can firstly be achieved by cross-linking individual avidin or streptavidin molecules so that so-called poly SA or homogeneously cross-linked SA is formed. SA in the following is always understood as avidin or streptavidin. Methods for cross-linking or polymerizing SA are known to a person skilled in the art. In particular a cross-linking by heat treatment or by bifunctional or polyfunctional compounds is suitable. Bifunctional or polyfunctional compounds are understood as molecules which carry at least two functional groups which can be the same or different and can react via these functional groups with functional groups of SA such as certain amino acid residues or carbohydrate residues. Typical examples of linkers suitable within the scope of the invention are listed in the following table 1.

TABLE 1

| Abbreviation | Chemical composition |
| --- | --- |
| SPDP | N-succinimidyl-3-(2-pyridyldithio)-propionate |
| EADP | ethyl 4-azidohenyl-1,4-dithiobutyrimidate.HCl |
| FNPA | 4-fluoro-3-nitrophenylazide |
| HSAB | N-hydroxysuccinimidyl-4-azidobenzoate |
| MABI | methyl-4-azidobenzoimidate.HCl |
| MBS | m-maleimidobenzoyl-N-hydroxysuccinimide ester |
| NHS-ASA | N-hydroxysuccinimidyl-4-azidosalicylic acid |
| MHS | maleimidohexanoyl-N-hydroxysuccinimide ester |
| PNP-DTP | p-nitrophenyl-2-diazo-3,3,3-trifluoropropionate |
| SADP | N-succinimidyl(4-azidophenyl)1,3'-dithiopropionate |
| SAND | sulfosuccinimidyl-2-(m-azido-o-nitrobenzamido)ethyl-1,3'-dithiopropionate |
| SANPAH | N-succinimidyl-6(4'-azido-2'-nitrophenyl-amino)hexanoate |
| SASD | sulfosuccinimidyl 2-(p-azidosalicylamido)ethyl-1,3'-dithiopropionate |
| SIAB | N-succinimidyl(4-iodoacetyl)aminobenzoate |
| SMCC | succinimidyl-4-(N-maleinimidoethyl)cyclohexane-1-carboxylate |
| SMPB | succinimidyl-4-(p-malainimidophenyl)butyrate |
| DSS | disuccinimidylsuberate |
| DMS | dimethylsuberimidate |
| Traut' reagent | 2-iminothiolane 2,4,6-trichloro-s-triazine |
| SAMBA | S'-acetyl-mercapto-succinic acid anhydride |
| SATP | N-succinimidyl-S-acetylthiopropionate |
| SATA | N-succinimidyl-S-acetylthioacetate |

Secondly the modification can be a coupling to other high molecular molecules in particular proteins such as bovine serum albumin (BSA) or immunoglobulin which are often used to reduce interference in immunoassays. This cross-linking leads to so-called heterogeneously cross-linked SA. In this process SA and/or the protein can in turn be polymerized in this complex. Methods for coupling SA to these molecules are known to a person skilled in the art. A coupling with DSS, SAMBA, SATP, MHS, SATA has proven to be particularly suitable. A complex of BSA and SA or poly SA is particularly suitable as an interference-eliminating agent. Even better effects are achieved when polymerized BSA is coupled to SA or poly SA. The polymerization or cross-linking of BSA can be achieved with the aforementioned methods for cross-linking SA. The most suitable is a polymerization by heat treatment as described in EP-A 0331 127.

Thirdly the modification of SA can be an inactivation of the active centres i.e. the binding sites for biotin. This results in the formation of so-called inactivated SA. The inactivation can be achieved by a simple saturation of the binding sites with biotin or with a biotin derivative which is bound by avidin or streptavidin. Due to the very high affinity of SA for biotin hardly any biotin which could eventually lead to interferences is released when used in the immunoassay. The active centre is preferably covalently modified. In this case one or several amino acid residues in the active centre of SA can be derivatized so that binding to biotin is greatly reduced or completely prevented. Methods for inactivating the biotin binding site in SA are known from Gitlin et al., Biochem. J. 269 (1990) 527–530. Tyrosine residues in the active centre of SA are preferably modified with p-nitrobenzenesulfonyl fluoride. A further method for inactivating the biotin binding site in SA is to covalently couple biotin to the binding site. Methods for coupling biotin to the active centre of SA are known to a person skilled in the art. A new method for coupling biotin to SA by means of a new photoactivatable biotin derivative has turned out to be particularly preferable. Photoactivatable biotin derivatives are known. In EP-A-0 155 854 and EP-A-0 187 323 azide-substituted phenyls/ nitrophenyls are described which are coupled by an amine-containing linker to biotin. Biotin-DADOO-AB (biotin-[8-(4-azidobenzoyl)-amino-3,6-dioxaoctyl]amide) is preferably used as the biotin derivative. Further biotin derivatives are described in the Boehringer Mannheim Biochemica catalogue order no. 1292633 and 1292641. After saturation of the biotin binding sites of SA with the biotin derivatives, the photoreaction is initiated and thus biotin is covalently fixed to the active centre. In this inactivated SA biotin is bound to the active centre and additionally bound outside the active centre via a covalent bond. The SA biotin product obtainable by this means is also a subject matter of the present invention.

A further method of inactivating the active centre of SA is to modify the binding sites by genetic engineering. The active centre of SA can be modified and inactivated by substitution, deletion or insertion of individual amino acid residues or short sections of amino acid residues. Preferably individual amino acids such as tyrosine residues are substituted by other amino acids in the active centre. It is, however, also possible to produce SA in which the binding site is partially or completely absent. Methods for modifying and producing SA by means of genetic engineering are known to a person skilled in the art. For example the production of recombinant streptavidin is described in EP-A-0 198 015.

Fourthly the modification can be achieved by a fragmentation of SA. The SA fragments can be produced by chemical or enzymatic cleavage or by recombinant production. In this case the biotin binding site in particular may be absent as already described above. The advantage of fragmentation is an improved solubility of the product. Preferably all fragments obtained by chemical or enzymatic cleavage from avidin or streptavidin are used in the mixture so that all or nearly all parts of SA are present.

The SA inactivated or fragmented in this way can be used in the aforementioned first or second method for modifying SA i.e. the inactivated SA can in turn be polymerized or cross-linked with other molecules such as BSA or poly BSA. These interference-eliminating agents in which a combination of at least two of the said methods have been carried out to modify the SA have proven to be particularly advantageous.

After the modification of SA by one of the said methods has been completed it is possible to remove remaining biotin binding activity, biotin covalently bound to the surface which is not bound in the active centre of avidin or streptavidin or free biotin by a suitable purification of the avidin or streptavidin derivatives. This can for example be achieved by adsorption to solid phase bound biotin and/or SA.

The invention therefore in addition concerns avidin or streptavidin derivatives obtainable by one of the methods described above for modification and subsequent purification to remove remaining biotin binding activity, biotin covalently bound to the surface which is not bound in the active centre of avidin or streptavidin or free biotin preferably by adsorption to a solid phase bound biotin and/or SA.

Furthermore the invention concerns a process for the production of the interference-eliminating agents according to the invention in which SA is modified according to at least one of the three aforementioned methods and is optionally subsequently purified as described above to remove remaining biotin binding capacity, biotin bound covalently to the surface or free biotin.

Avidin or streptavidin or derivatives thereof can be used to reduce interference in all common immunoassays or nucleic acid assays. They are particularly suitable for reducing interference in immunoassays or nucleic acid assays in which avidin or streptavidin is used as a binding component. Such immunoassays are for example known from Guesdon et al., J. Histochem. Cytochem. 27 (1979) 1131–1139 and Bayer and Wilchek, Analytical Biochemistry 171 (1988) 1–32. The interferences can for example be caused by antibodies against avidin or streptavidin which sometimes occur in human serum. However, the interference-eliminating agent according to the invention also exhibits an advantageous effect in immunoassays in which no avidin or streptavidin is used. In these immunoassays the use of SA which is bound to a further molecule such as for example BSA or poly BSA corresponding to the second method of modification described above has proven to be particularly advantageous in these immunoassays. The interference-eliminating agent according to the invention is always used in addition to the reagents that are otherwise necessary in the test. It is not identical to the avidin or streptavidin components which may possibly be present in the test such as an SA-coated solid phase or enzyme-SA conjugates. In contrast to these SA reagents the interference-eliminating reagent according to the invention is not incorporated into the complex to be detected composed of analyte and specific binding partners.

The invention furthermore concerns a method for the determination of an analyte in a sample by
(1) contacting the sample with
    (a) avidin or streptavidin or a derivative thereof
    (b) one or several specific binding partners of the analyte and
(2) measuring the complex formed from analyte and specific binding partners as a measure for the presence of the analyte.

All substances can serve as the analyte which react to form a complex with at least one specific binding partner such as for example haptens, antigens, antibodies or nucleic acids. The method according to the invention is particularly suitable for the detection of antibodies in particular autoantibodies.

In general body fluids such as blood, plasma, serum, saliva or urine serve as the sample.

Any biological or chemical binding partners can serve as the specific binding partner which is capable of specifically binding the analyte and can form a complex with it. These include antibodies, antibody fragments, antigens, haptens, hormones, avidin, biotin, nucleic acids, oligonucleotides or derivatives thereof. Antibodies or antigens or fragments thereof are preferably used in the present invention as a binding partner of the analyte.

In order to detect the complex composed of analyte and specific binding partner it is possible to use all methods familiar to a person skilled in the art. It is possible to use homogeneous methods in which all binding partners in the method are in a soluble form such as precipitation methods with a turbidimetric or nephelometric determination of the complex formed or immunoassays based on the Cloned Enzyme Donor Immunoassay (CEDIA), enzyme multiplied immunoassay technique (EMIT), or fluorescence polarization immunoassay (FPIA) principle. Heterogeneous methods are also suitable in which at least one reagent is bound to a solid phase. Examples of this are agglutination tests in which one partner of a binding pair is for example bound to latex, sandwich assays, Enzyme Liked Immunoassay ELISA for the detection of specific antibodies such as e.g. against HIV, HCV, rubella, toxoplasma gondii, glutamate decarboxylase or thyroglobulin, RIA or immunometric assays. Apart from the precipitation methods, one of the specific binding partners is labelled in all these methods. The label can directly generate a measurable signal which is for example a radioisotope, a chemiluminescent, fluorescent or electrochemiluminescent label or a coloured particle such as a metal sol particle or dyed or undyed latex. The label can also generate an indirect signal such as an enzyme label like peroxidase, glucose oxidase, $\beta$-galactosidase or alkaline phosphatase.

The immunoassays can also be carried out by means of test strips or biosensors in particular when one of the binding partners is coupled via SA to the solid phase. Interference in immunoassays based on the principle plasmon resonance can also be reduced according to the invention.

One reagent of the method for detecting the analyte is often coupled via a specific binding pair such avidin or streptavidin/biotin to the solid phase. The advantage of this is that the solid phase can be used universally in several test procedures. It is also possible to bind the label to a component of the assay via a specific binding pair. For example an enzyme can be coupled to avidin or streptavidin and the binding partner, for example an antibody, can be biotinylated. Examples of such test procedures are known to a person skilled in the art. The avidin or streptavidin derivative according to the invention is particularly suitable for reducing interference in those methods of detection which utilize an indirect binding of a reaction component by avidin/biotin or streptavidin/biotin.

The method for detecting the analyte can be carried out in one or several steps i.e. the incubation of the analyte with the individual test components can be carried out simultaneously or successively. If avidin or streptavidin or a derivative thereof is used in which the biotin binding sites have not been inactivated, then in methods in which a binding component is coupled via avidin/biotin or streptavidin/biotin care must be taken that binding of the binding components via avidin/biotin or streptavidin/biotin is already completed before avidin or streptavidin or a derivative thereof is added since otherwise the non-inactivated biotin binding sites would bind to the biotinylated binding component and cause interferences. For example when using an avidin or streptavidin solid phase, the biotinylated specific binding partner of the analyte must be added first before the sample is added together with avidin or streptavidin or a derivative thereof. If an avidin or streptavidin derivative according to the invention is used in which the biotin binding sites have been inactivated then all test reagents can be incubated simultaneously since the biotinylated reagents do not bind to the avidin or streptavidin derivative. This inactivated avidin or streptavidin derivative can thus be used universally in all conceivable test variants and is thus preferred.

The concentration of the interference-eliminating agent according to the invention in the test mixture is between 0.0001 and 1% (m/v) preferably between 0.01 and 1% (m/v).

The individual reaction components of the method for detecting the analyte are advantageously offered in the form of a test combination or a test kit. Therefore a further subject matter of the invention is a test combination for a method for detecting an analyte in a sample containing avidin or streptavidin or a derivative thereof and at least one specific binding partner of the analyte. In addition it can also contain all other reagents necessary to carry out the test procedure such as buffers, detergents, labels, auxiliary substances to detect the label such as enzyme substrates, solid phases etc. The interference-eliminating agent according to the invention and the binding partner or binding partners of the analyte are preferably packaged in separate containers. If an interference-eliminating agent according to the invention is used in which the biotin binding site has been inactivated, the interference-eliminating agent can also be added directly to the binding partners of the analyte.

EXAMPLE 1

Production of polymeric streptavidin

Figure 1:
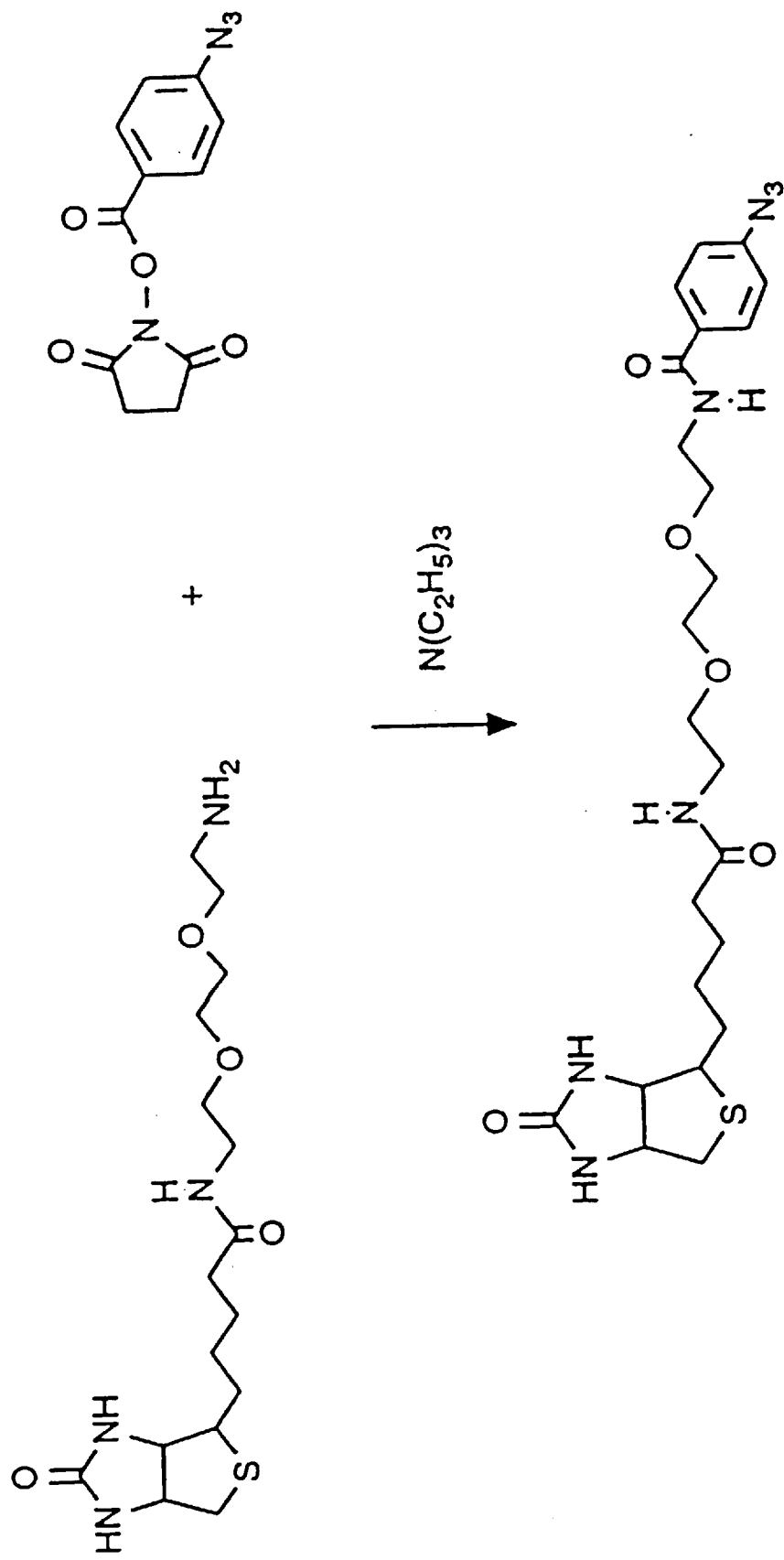
FIG. 1 shows the synthetic path of biotin-DADOO-AB. The invention is elucidated by the following examples.

Polymerized streptavidin is produced according to EP-A-0 331 127.

Activation of streptavidin with maleimido-hexanoyl-N-hydroxysuccinimide ester 30 mg streptavidin is dissolved in 3 ml 30 mM potassium phosphate/100 mM sodium chloride (pH 7.1) and heated to 25° C. 0.15 ml maleinimido-hexanoyl-N-hydroxysuccinimide ester (MHS) (Boehringer Mannheim GmbH) in DMSO (10 mg/ml) is added dropwise while stirring. After a reaction time of 1 hour at 25° C. the solution is cooled in an ice bath. Subsequently the MHS-streptavidin which is formed is twice dialysed at 4° C. against 1 liter 50 mM potassium phosphate/100 mM sodium chloride (pH 5.0).

Activation of streptavidin with S-acetylmercaptosuccinic acid anhydride 30 mg streptavidin is dissolved in 3 ml 100 mM potassium phosphate (pH 7.8) and heated to 25° C. 0.175 ml S-acetylmercaptosuccinic acid anhydride (SAMBA) in DMSO (10 mg/ml) is added dropwise while stirring. After a reaction time of 3 hours at 25° C. the SAMBA-streptavidin which is formed is twice dialysed at 4° C. against 1 liter 50 mM potassium phosphate/2 mM EDTA (pH 6.5).

Homogeneous cross-linkage of streptavidin 3 ml of a solution of activated SAMBA-streptavidin (10 mg/ml) is heated to 25° C. and admixed with 50 μl 1 M hydroxylamine (pH 6.5). After 30 minutes at 25° C. it is diluted by addition of 15 ml 50 mM potassium phosphate/100 mM sodium chloride/1 mM EDTA (pH 6.5). The homogeneous cross-linkage of streptavidin is started by addition of 3 ml activated MHS-streptavidin (10 mg/ml). After a reaction time of 2 hours at 25° C. while carefully stirring, the reaction is terminated by adding 0.2 ml 100 mM cysteine/HCl. After an incubation time of 30 minutes at 25° C. the pH value of the solution is adjusted to 7.5 by addition of 1 M dipotassium hydrogen phosphate. After addition of 0.2 ml 500 mM iodacetamide it is incubated for a further hour at 25° C. Afterwards it is dialysed twice at 4° C. against 3 litres 50 mM potassium phosphate/100 mM sodium chloride (pH 7.5). The conjugate is concentrated in an ultrafiltration cell after dialysis and lyophilized after addition of sucrose (8%).

EXAMPLE 2

Production of thermo-BSA-SA

Thermo-BSA streptavidin (thermo-BSA-SA) is produced according to EP-A-0 331 127.

Cross-linking BSA to thermo-BSA 1.0 g BSA is dissolved in 100 ml 20 mM potassium phosphate buffer pH 7.0 and kept at a temperature of 70° C. for 5 hours. Subsequently it is cooled to 20° C. and dialysed against 100 mM potassium phosphate buffer pH 7.8.

Activation of thermo-BSA with SAMBA 68 mg thermo-BSA is dissolved in 2 ml 0.1 M potassium phosphate buffer pH 7.8 and it is slowly admixed with 0.38 ml SAMBA (10 mg/ml in DMSO). After a reaction time of 3.5 hours at 25° C. it is dialysed at 4° C. against 1 liter 50 mM potassium phosphate buffer pH 6.5.

Production of a thermo-BSA-streptavidin conjugate

The heterogeneous cross-linking of streptavidin with thermo-BSA is carried out analogously to the homogeneous cross-linking described in example 1. In this process 60 mg activated MHS-streptavidin (produced according to example 1) is reacted with 68 mg SAMBA-thermo-BSA. The reaction product is purified by means of gel filtration (Superose 6 prep. grade) and concentrated in an ultrafiltration cell. The product obtained is subsequently lyophilized.

EXAMPLE 3

Saturation of thermo-BSA-SA with free biotin 60 mg thermo-BSA-SA dissolved in 6.0 ml potassium phosphate buffer, 100 mM pH 7.0 is admixed with 2 mg D-biotin dissolved in 0.5 ml potassium phosphate buffer, 10 mM pH 7.8 and stirred for 1 hour.

The free biotin is separated by means of gel filtration (Superose 6). The high molecular protein fraction is dialysed against 10 mM potassium phosphate buffer, pH 7.0 and lyophilized after addition of 8% sucrose.

EXAMPLE 4

Production of covalently-modified streptavidin

Tyrosine residues in the active centre of streptavidin/avidin are derivatized with p-nitrobenzene-sulfonyl fluoride according to G. Gitlin, E. A. Bayer, M. Wilchek: Studies on the biotin-binding sites of Avidin and Streptavidin; Biochem. J. (1990), 269, 527–530.

A 200-fold molar excess of p-nitro-benzenesulfonyl fluoride (Sigma N-2262) relative to the streptavidin subunit is added to 1 g streptavidin at a protein concentration of 10 mg/ml in 0.1 M Tris-HCl buffer, pH 7.9. After the addition it is stirred for a further 18–20 hours at 25° C. The product is then dialysed against >500-fold volume PBS buffer pH 7.5 (16–18 hours at 40°) in order to separate non-reacted derivatization reagent.

EXAMPLE 5

Production of photoactivatable biotin Synthesis of biotin-[8-(4-azidobenzoyl)amino-3,6-dioxaoctyl] amide (biotin-DADOO-AB)

1.50 g (4 mmol) biotinoyl-1,8-diamino-3,6-dioxaoctane (biotin-DADOO, Boehringer Mannheim GmbH) is dissolved in 50 ml freshly distilled DMF while stirring. 1.04 g (4 mmol) N-hydroxysuccinimidyl-(4-azidobenzoate) (HSAB, Boehringer Mannheim GmbH) and 0.55 ml (4 mmol) triethylamine is successively added to the solution and allowed to stir for 2 hours at 20° C. Subsequently the solvent is removed on a rotary evaporator in an oil pump vacuum and the crude product that remains is purified by chromatography on silica gel. For this it is dissolved in as small amount as possible of chloroform/methanol 2/1 (v/v)

while heating slightly to ca. 40° C. and applied to a silica gel 60 (Merck Company, Germany) column (4×60 cm). It is eluted with chloroform/methanol 2/1 (v/v) and fractions of 50 ml are pooled. The fractions containing the pure product are determined by means of TLC (system as described below) and pooled. The solvent is removed on a rotary evaporator and the semi-solid residue is digested with ca. 50 ml diisopropyl ether. The finely crystalline, colourless product is suction filtered and dried overnight in a vacuum drying oven (0.1–0.15 bar/40° C.).

Yield: 1.24 g (60% of theory) TLC: silica gel 60 (Merck) $F_{254}$, chloroform/methanol 2/1 (v/v); $R_f$=0.71. $^1$H-NMR (100MHz/d6-DMSO:δ (ppm)=1.20–1.65 (m,6H) ; 2.07 (tr, 2H); 2.60–3.65 (m,15H); 4.05–4.20 (m;2H); 6.38 (d,br, 2H), 7.20 (d, 2H), 7.62 (tr,br, 1H); 7.91 (d, 2H); 8.53 (tr,br, 1H). UV (CH$_3$OH): λ(max)=267nm; IR(KBr): υ=2125 cm$^{-1}$ The synthetic path of biotin-DADOO-AB is shown in FIG. 1.

EXAMPLE 6

Production of biotin(photoactivated) streptavidin

Streptavidin is reacted with a photoactivatable biotin derivative (e.g. biotin-DADOO-AB) and dialysed to remove free unbound biotin. The photoreaction is initiated by irradiation with a Hg vapour lamp (350–700 nm) and the biotin is covalently immobilized in the binding centre of streptavidin.

A 10-fold molar excess of biotin-DADOO-AB reagent (3.5 ml of a 25 mg/ml biotin-DADOO-AB stock solution in DMSO) is added to 1 g streptavidin at a protein concentration of 20 mg/ml in PBS buffer pH 7.5. After the addition it is stirred for 2 hours at 25° C. with exclusion of light.

Free unbound biotin derivative is completely separated (no longer detectable) by dialysis (20 hours, 4° C.) against a >500-fold volume of PBS buffer, pH 7.5 with exclusion of light. The mixture is then irradiated for 20 min with a <5 cm path length of the solution using a Hg vapour lamp (350–700 nm) while stirring and subsequently dialysed again against a >500-fold volume of PBS buffer, pH 7.5 (16–18 hours, 4° C.).

EXAMPLE 7

Purification of inactivated streptavidin and thermo-BSA-SA and derivatives and fragments thereof Production of BSA-biotin adsorber A 10-fold molar excess of D-biotinoyl-ε-aminocaproic acid-N-hydroxysuccinimide ester (Boehringer Mannheim GmbH) was added to 1 g BSA at a protein concentration of 10 mg/ml in PBS buffer, pH 8.5.

After the addition it is stirred for 2 hours at 25° C. and the reaction is stopped by addition of lysine to a final concentration of 10 mM. Free unbound biotin derivative is completely separated (no longer detectable) by dialysis (16–18 h, 4° C.) against a >500-fold volume of PBS buffer, pH 7.5.

300 ml glutaric dialdehyde (10%) is added to 40 g amino-Spherosil (Boehringer Mannheim GmbH) and the mixture is stirred for 2 hours at pH 3.7 and 55° C. while rotating. The suspension is washed with >7 Spherosil volumes of redistilled water and 5 Spherosil volumes of PBS buffer, pH 8.0. The activated Spherosil is subsequently reacted with BSA-Bi for 20 hours at room temperature with a protein supply of 5–10 mg/ml Spherosil while shaking.

The unreacted protein solution is separated over a glass suction filter and the adsorber material is washed with 10 Spherosil volumes 0.9% NaCl solution and incubated for 1 hour with 5 Spherosil volumes of ethanolamine solution.

The adsorber material is then washed with a 5-fold Spherosil volume of 0.9% NaCl solution, washed with a 3-fold Spherosil volume of 1M propionic acid and enough 30 mM NaCl solution to reach a pH of 6.5. The adsorber is adequately equilibrated with PBS buffer pH 7.5.

Production of streptavidin-Spherosil adsorber 300 ml glutaric dialdehyde (10%) is added to 40 g amino-Spherosil (Boehringer Mannheim GmbH) and the mixture is stirred for 2 hours at pH 3.7 and 55° C. while rotating. The suspension is washed with >7 Spherosil volumes of redistilled water and 5 Spherosil volumes of PBS buffer, pH 8.0. The activated Spherosil is subsequently reacted with streptavidin for 20 hours at room temperature with a protein supply of 5–10 mg/ml Spherosil (Boehringer Mannheim GmbH) while shaking.

The unreacted protein solution is separated over a glass suction filter and the adsorber material is washed with 10 Spherosil volumes of 0.9% NaCl solution and incubated for 1 hour with 5 volumes ethanolamine solution. The adsorber material is then washed with the 5-fold Spherosil volume of 0.9% NaCl solution, with the 3-fold Spherosil volume of 1M propionic acid and enough 30 mM NaCl solution to reach a pH of 6.5. The adsorber is adequately equilibrated with PBS buffer pH 7.5.

Inactivated streptavidin is purified of streptavidin with residual activity (biotin binding), residual free biotin or streptavidin having biotin that is covalently accessible on the surface (in contrast to biotin immobilized in the binding pocket) according to example 3, 4 or 6 by means of chromatography on a bovine serum albumin-biotin and/or streptavidin adsorber based on Spherosil.

1 ml streptavidin-Spherosil adsorber, equilibrated in PBS buffer pH 7.5, is added to the reaction mixture per 10 mg protein and stirred for 2 hours at 25° C.

The suspension is then transferred to a column and the column material is washed with PBS buffer pH 7.5. In this process the protein content is monitored at the outlet of the column via a UV monitor at $A_{280nm}$. It is washed until free of protein. The eluant containing protein is collected in a fraction.

1 ml bovine serum albumin-biotin (BSA-Bi)-Spherosil adsorber, equilibrated in PBS buffer, pH 7.5 is added per 10 mg protein to the eluant of the streptavidin adsorber containing protein and it is stirred for 2 hours at room temperature.

The suspension is transferred to a column and washed with PBS buffer, pH 7.5. In this process the protein content is monitored at the outlet of the column via a UV monitor at $A_{280nm}$. The eluant containing protein contains the product and is collected as a fraction. The product (inactivated (poly)streptavidin or thermo-BSA-SA or derivatives and fragments thereof) is concentrated to a protein concentration of 20 mg/ml and lyophilized after dispensing.

EXAMPLE 8

Carrying out a GAD antibody test in a sequential test procedure with regard to biotinylated antigen and sample 100 μl biotinylated glutamate decarboxylase (GAD) isolated from pig brain is pipetted at an optimal concentration for each of the respective batches (1–3 μg/ml in the incubation buffer from the Boehringer Mannheim Enzymun Test® Anti-HIV 1+2) into each well of a microtitre plate precoated with thermo-BSA streptavidin and incubated for 30 min at room temperature. Afterwards the plate is washed three times with 350 μl 50 mmol/l potassium phosphate, pH 7.0 with addition of 0.1% (w/v) CHAPSO (3-[3-cholamidopropyl)-dimethylammonio]-2-hydroxy-1-propanesulfonate) each time. Human serum is diluted 1+25 in incubation buffer from the Enzymun Test® anti-HIV 1+2 to which the respective amount of thermo-BSA-streptavidin (untreated or inactivated) or streptavidin monomer or streptavidin polymer (untreated or inactivated) was added. These samples diluted in this way are incubated for 1 hour at room temperature in the microtitre plate in a volume of 100 μl/well while shaking. Subsequently the samples are aspirated and the plates are washed three times as above. The POD-coupled detection antibody from sheep with a binding specificity for human IgG is diluted in conjugate buffer from the Enzymun Test® anti-HIV 1+2 to a concentration of 75 mU/ml and 100 μl of this diluted solution is incubated in each well for 1 hour at room temperature while shaking at room temperature. The liquid is aspirated and the plate is again washed 3 times as above. The dye ABTS® is dissolved to a concentration of 1 mg/ml in the Enzymun Tests® substrate buffer and 100 μl/well is incubated at room temperature without shaking. After ca. 30 min the absorbance is read in a microtitre plate photometer. The measuring wavelength is 405 nm and the reference wavelength is 492 nm. The blank is two untreated wells which only contain substrate/dye solution. The mean value of the absorbance of the two blank wells is deducted from all other absorbances.

The mean values of a sample determined in duplicate from two wells are listed as absorbances in tables 2, 3 and 4.

TABLE 2

Interference elimination by addition of various amounts of thermo-BSA streptavidin

| Sample | Absorbance without addition to buffer | Signal level in % of the initial signal with the respective amount of thermo-BSA-SA (% w/v) | | | | | | | |
|---|---|---|---|---|---|---|---|---|---|
| | | 0 | 0.01 | 0.025 | 0.05 | 0.1 | 0.25 | 0.5 | 1 |
| buffer | 0.016 | * | * | * | * | * | * | * | * |
| normal serum | 0.182 | 100 | 95 | 68 | 71 | 74 | 70 | 70 | 60 |
| positive control (MICA) | 1.906 | 100 | 72 | 74 | 73.5 | 73 | 65 | 62 | 44 |
| positive serum | 2.065 | 100 | 63 | 61 | 62 | 60 | 50 | 48 | 37 |
| interference serum 1 | 2.325 | 100 | 16 | 14 | 15 | 16 | 15 | 14 | 11 |
| interference serum 2 | 1.243 | 100 | 9 | 8.5 | 8 | 5 | 4 | 4 | 2 |
| interference serum 3 | 0.707 | 100 | 24 | 16 | 13 | 13 | 10 | 10 | 8 |

*not listed because inappropriate due to the low measured signal.
MICA: monoclonal antibody against GAD

TABLE 3

Interference elimination by addition of monomeric or polymeric streptavidin

| Sample | without addition | 1% (w/v) SA | 1% (w/v) polySA |
|---|---|---|---|
| buffer | 0.008 | 0.006 | 0.009 |
| normal serum | 0.106 | 0.144 | 0.108 |

TABLE 3-continued

Interference elimination by addition of monomeric or polymeric streptavidin

| Sample | without addition | 1% (w/v) SA | 1% (w/v) polySA |
|---|---|---|---|
| interference serum | 1.390 | 0.108 | 0.087 |
| positive control (MICA) | 0.950 | 1.588 | 1.033 |
| positive serum | 0.940 | 1.416 | 0.950 |

TABLE 4

Interference elimination by addition of thermo-BSA-streptavidin or thermo-BSA-streptavidin which had been covalently modified (according to example 40

| Sample | without addition | 0.025% (w/v) thermo-BSA-SA | 0.025% (w/v) thermo-BSA-SA (inact.) |
|---|---|---|---|
| buffer | 0.009 | 0.011 | 0.011 |
| normal serum | 0.226 | 0.191 | 0.206 |
| interference serum | 1.500 | 0.117 | 0.332 |
| positive control (MICA) | 1.745 | 1.528 | 1.579 |
| positive serum | 1.963 | 1.457 | 0.797 |

EXAMPLE 9

Elimination of interference in an anti-HCV test using biotin(photoactivated)-SA

Test principle:

2-Step sandwich assay with a streptavidin solid phase (test procedure and reagents as in the Boehringer Mannheim Enzymun Test® anti-HIV 1+2)

1st Step: biotinylated peptides plus sample

2nd Step: reaction of wall-bound antibody with an anti-human IgG-POD conjugate

3rd Step: indicator reaction with ABTS as the substrate

Buffer:

a) Incubation buffer from the Enzymun Test® anti-HIV 1+2 HCV peptides from the core, NS4 and NS5 region ± inactivated streptavidin prepared according to example 6 and 7
b) Conjugate buffer from the Enzymun Test® anti-HIV 1+2
Incubation periods:
1st Step: 1 hour (sample+incubation buffer)
2nd Step: 1 hour (+conjugate buffer)
3rd Step: 1 hour (substrate reaction with ABTS)
Samples:
3 negative serum samples (reference 1)
6 false-positive anti-HCV negative samples
3 positive anti-HCV samples (reference 2)
Volumes:
sample 20 µl
all other reagents 500 µl of each
Test procedure:
On an ES 600 at 25° C. according to the test instructions the Enzymun Test® anti-HIV 1+2
Substrate measurement:
Measurement of the substrate solution at 422 nm on an ES 600 (Boehringer Mannheim GmbH). The absorbances are listed in table 5.

TABLE 5

| Samples | without ianct. SA in incubation buffer | 20 µg/ml inact. SA in incubation buffer | decrease in signal after addition of inact. SA |
|---|---|---|---|
| negative serum 1 | 0.036 | 0.027 | * |
| negative serum 2 | 0.042 | 0.035 | * |
| negative serum 3 | 0.078 | 0.076 | * |
| HCV negative serum 1 | 0.528 | 0.125 | 76% |
| HCV negative serum 2 | 0.467 | 0.106 | 77% |
| HCV negative serum 3 | 0.979 | 0.161 | 84% |
| HCV negative serum 4 | 0.499 | 0.094 | 81% |
| HCV negative serum 5 | 2.049 | 0.471 | 77% |
| HCV negative serum 6 | 0.427 | 0.065 | 85% |
| HCV positive serum 1 | 1.747 | 1.645 | 6% |
| HCV positive serum 2 | 1.161 | 1.076 | 7% |
| HCV positive serum 3 | 1.104 | 1.026 | 7% |

*not stated, inappropriate due to the low measured signal.

We claim:

1. A method for reducing nonspecific interactions in an assay for the determination of an analyte in a sample, comprising contacting a sample with (a) an interference elimination agent selected from the group consisting of avidin, streptavidin and interference reducing derivatives thereof, wherein said interference elimination agent is modified to inactivate any biotin binding capacity and (b) at least one specific binding partner of the analyte, and
   measuring any complex formed between the analyte and said specific binding partner as a measure for the determination of the analyte,
   wherein said interference elimination agent is not incorporated into the complex formed between the analyte and said specific binding partner.

2. The method according to claim 1, wherein the sample is simultaneously contacted with (a) and (b).

3. The method according to claim 1, wherein said interference elimination agent is homogeneously cross-linked avidin or streptavidin molecules.

4. The method according to claim 1, wherein said interference elimination agent is avidin or streptavidin cross-linked by bifunctional or polyfunctional compounds.

5. The method according to claim 1, wherein said interference elimination agent is heterogeneous cross-linked avidin or streptavidin molecules.

6. The method according to claim 5, wherein said interference elimination agent is avidin or streptavidin molecules cross-linked with proteins.

7. The method according to claim 5, wherein said interference elimination agent is avidin or streptavidin molecules cross-linked with polymerized proteins.

8. The method according to claim 1, wherein said interference elimination agent is fragments or a mixture of fragments of an avidin or streptavidin molecule, wherein said fragments retain the interference-eliminating effect of the entire avidin or streptavidin molecule, and wherein said avidin or streptavidin is fragmented and all fragments obtained are present in a mixture as said interference elimination agent.

9. The method according to claim 1, wherein said interference elimination agent is inactivated avidin or streptavidin.

10. The method according to claim 9, wherein the inactivation of avidin or streptavidin is carried out by saturation with biotin or a biotin derivative.

11. The method according to claim 9, wherein the inactivation is achieved by covalently modifying the active center of avidin or streptavidin.

12. The method according to claim 11, wherein the covalent modification is carried out by derivatizing at least one amino acid of the active center or covalently coupling biotin to the active center.

13. The method according to claim 12, wherein said covalently coupled biotin is photoactivatable biotin.

14. The method according to claim 13, wherein said photoactivatable biotin is biotin-DADOO-AB.

15. The method according to claim 9, wherein the active center is deactivated by genetic engineering methods selected from the group consisting of substitution of tyrosine residues, deletion of tyrosine residues and deletion of the binding site.

16. The method according to claim 9, wherein the inactivated avidin or streptavidin is purified over solid phase bound streptavidin, biotin, avidin or a combination of biotin and avidin.

17. The method according to claim 1, wherein said interference elimination agent is present in a concentration of between 0.0001 to 1% m/v.

18. The method according to claim 17, wherein said interference elimination agent is present in an amount between 0.01 to 1% m/v.

19. The method according to claim 1, wherein said assay for the presence of an analyte in a sample is an immunoassay or a nucleic acid assay in which avidin or streptavidin is used as a binding component.

20. A test kit for determining an analyte in a sample, comprising
   a) at least one specific binding partner of the analyte, and
   b) an interference elimination agent selected from the group consisting of inactivated avidin, inactivated streptavidin and interference reducing derivatives thereof, wherein the active center of said inactivated avidin or inactivated streotavidin is saturated with a photoactivatable biotin derivative, and said photoactivatable biotin derivative is additionally bound outside the active center of said inactivated avidin or inactivated streptavidin via a covalent bond, wherein said photoactivatable biotin is covalently coupled by initiating the photoreaction.

21. The test kit according to claim 20, further comprising one or more reagents selected from the group consisting of buffers, detergents, labels, auxiliary substances to detect the label and a solid phase.

22. The test kit according to claim 20, wherein said interference eliminating agent and said specific binding partner of the analyte are in separate containers.

23. A process for the production of an interference eliminating agent, comprising modifying avidin or streptavidin such that said avidin or streptavidin cannot be incorporated into a complex formed between an analyte and a specific binding partner for said analyte, wherein a photoactivatable biotin derivative is bound to the active center and is additionally bound outside the active center via a covalent bond, wherein said avidin or streptavidin is modified by saturating the active center with a photoactivatable biotin derivative and photoactivatable biotin is additionally bound outside the active center of said avidin or streptavidin via a covalent bond and thereafter covalently coupling the biotin derivative by initiating the photoreaction.

24. An inactivated avidin or streptavidin wherein the active center of said avidin or streptavidin is saturated with biotin or a biotin derivative and said avidin or streptavidin is purified over streptavidin, biotin, avidin, or a combination of biotin and avidin bound to a solid phase, wherein the active center of said avidin or streptavidin is saturated with a photoactivatable biotin derivative, and photoactivatable biotin is additionally bound outside the active center of said avidin or streptavidin via a covalent bond, wherein said biotin is covalently coupled by initiating the photoreaction.

25. The inactivated avidin or streptavidin as claimed in claim 24, wherein said photoactivatable biotin derivative is biotin-DADOO-AB.

* * * * *